US 6,991,644 B2

(12) United States Patent
Spooner et al.

(10) Patent No.: US 6,991,644 B2
(45) Date of Patent: Jan. 31, 2006

(54) METHOD AND SYSTEM FOR CONTROLLED SPATIALLY-SELECTIVE EPIDERMAL PIGMENTATION PHOTOTHERAPY WITH UVA LEDS

(75) Inventors: Greg Spooner, Kensington, CA (US); Dean A. MacFarland, Magnolia, MA (US); David A. Gollnick, San Francisco, CA (US)

(73) Assignee: Cutera, Inc., Brisbane, CA (US)

( * ) Notice: Subject to any disclaimer, the term of this patent is extended or adjusted under 35 U.S.C. 154(b) by 0 days.

(21) Appl. No.: 10/728,527

(22) Filed: Dec. 5, 2003

(65) Prior Publication Data

US 2004/0116984 A1 Jun. 17, 2004

Related U.S. Application Data

(60) Provisional application No. 60/432,935, filed on Dec. 12, 2002.

(51) Int. Cl.
*A61N 5/06* (2006.01)

(52) U.S. Cl. .............................. 607/88; 128/898; 606/9
(58) Field of Classification Search ............ 607/88–89; 128/898
See application file for complete search history.

(56) References Cited

U.S. PATENT DOCUMENTS

| 3,538,919 | A | 11/1970 | Meyer | 606/36 |
|---|---|---|---|---|
| 3,693,623 | A | 9/1972 | Harte et al. | 606/9 |
| 3,834,391 | A | 9/1974 | Block | 606/9 |
| 3,900,034 | A | 8/1975 | Katz et al. | 607/89 |
| 4,122,853 | A | 10/1978 | Smith | 606/4 |
| 4,388,924 | A | 6/1983 | Weissman et al. | 606/9 |
| 4,461,294 | A | 7/1984 | Baron | 606/5 |
| 4,608,978 | A | 9/1986 | Rohr | 606/9 |
| 4,617,926 | A | 10/1986 | Sutton | 606/9 |
| 4,733,660 | A | 3/1988 | Itzkan | 606/9 |
| 4,819,669 | A | 4/1989 | Politzer | 132/200 |
| 4,829,262 | A | 5/1989 | Furumoto | 359/346 |
| 4,917,084 | A | 4/1990 | Sinofsky | 606/7 |
| 4,930,504 | A | 6/1990 | Diamantopoulos et al. | 128/395 |
| 5,000,752 | A | 3/1991 | Hoskin et al. | 606/9 |
| 5,057,104 | A | 10/1991 | Chess | 606/9 |
| 5,059,192 | A | 10/1991 | Zaias | 606/9 |
| 5,090,798 | A | 2/1992 | Kohayakawa | 351/221 |
| 5,178,617 | A | 1/1993 | Kuizenga et al. | 606/17 |
| 5,182,857 | A | 2/1993 | Simon | 30/34.05 |
| 5,217,455 | A | 6/1993 | Tan | 606/9 |
| 5,226,907 | A | 7/1993 | Tankovich | 606/133 |
| 5,258,989 | A | 11/1993 | Raven | 372/6 |
| 5,259,380 | A | 11/1993 | Mendes et al. | 607/115 |

(Continued)

FOREIGN PATENT DOCUMENTS

EP 736 308 A2 10/1996

(Continued)

OTHER PUBLICATIONS

R. Anderson, *Harvard Medical School, Reprint* "Clinical Use of the LightSheer Diode Laser System," Mar. 1998, 5 pages in length.

(Continued)

*Primary Examiner*—Henry M Johnson, III
(74) *Attorney, Agent, or Firm*—Stallman & Pollock LLP

(57) ABSTRACT

The invention comprises a system and method for treating an exposed tissue of a patient with a light energy. A plurality of light emitting devices are optically coupled with a patients tissue, and apply light treatments to the tissue. A driver circuit and a controller operate to drive the light emitting devices to output different intensities of light treatment to different sub-areas of the tissue being treated.

13 Claims, 5 Drawing Sheets

U.S. PATENT DOCUMENTS

| | | | | |
|---|---|---|---|---|
| 5,282,797 | A | 2/1994 | Chess | 606/9 |
| 5,290,273 | A | 3/1994 | Tan | 606/9 |
| 5,304,170 | A | 4/1994 | Green | 606/9 |
| 5,312,395 | A | 5/1994 | Tan et al. | 606/9 |
| 5,344,418 | A | 9/1994 | Ghaffari | 606/9 |
| 5,358,503 | A * | 10/1994 | Bertwell et al. | 606/27 |
| 5,397,327 | A | 3/1995 | Koop et al. | 606/17 |
| 5,405,368 | A | 4/1995 | Eckhouse | 607/88 |
| 5,425,728 | A | 6/1995 | Tankovich | 606/9 |
| 5,474,549 | A | 12/1995 | Ortiz et al. | 606/9 |
| 5,486,172 | A | 1/1996 | Chess | 606/20 |
| 5,500,009 | A | 3/1996 | Mendes et al. | 607/88 |
| 5,505,726 | A | 4/1996 | Meserol | 606/9 |
| 5,522,813 | A | 6/1996 | Trelles | 606/2 |
| 5,527,350 | A | 6/1996 | Grove et al. | 607/89 |
| 5,531,740 | A * | 7/1996 | Black | 606/9 |
| 5,549,660 | A | 8/1996 | Mendes et al. | 607/88 |
| 5,611,795 | A | 3/1997 | Slatkine et al. | 606/9 |
| 5,616,140 | A | 4/1997 | Prescott | 606/10 |
| 5,620,478 | A | 4/1997 | Eckhouse | 607/88 |
| 5,626,631 | A | 5/1997 | Eckhouse | 607/88 |
| 5,630,811 | A | 5/1997 | Miller | 606/9 |
| 5,658,323 | A | 8/1997 | Miller | 606/89 |
| 5,683,380 | A | 11/1997 | Eckhouse et al. | 606/9 |
| 5,735,844 | A | 4/1998 | Anderson et al. | 606/9 |
| 5,738,679 | A | 4/1998 | Daikuzono | 606/11 |
| 5,743,901 | A | 4/1998 | Grove et al. | 606/9 |
| 5,800,479 | A | 9/1998 | Thiberg | 607/88 |
| 5,820,625 | A | 10/1998 | Izawa et al. | 606/9 |
| 5,944,748 | A | 8/1999 | Mager et al. | 607/88 |
| 5,957,960 | A | 9/1999 | Chen et al. | 607/92 |
| 5,964,749 | A | 10/1999 | Eckhouse et al. | 606/9 |
| RE36,634 | E | 3/2000 | Ghaffari | 606/9 |
| 6,063,108 | A | 5/2000 | Salansky et al. | 607/89 |
| 6,080,147 | A | 6/2000 | Tobinick | 606/9 |
| 6,106,514 | A | 8/2000 | O'Donnell, Jr. | 606/9 |
| 6,159,236 | A | 12/2000 | Biel | 607/92 |
| 6,210,425 | B1 | 4/2001 | Chen | 607/88 |
| 6,228,075 | B1 | 5/2001 | Furumoto | 606/9 |
| 6,238,424 | B1 * | 5/2001 | Thiberg | 607/88 |
| 6,238,425 | B1 | 5/2001 | Thiberg | 607/88 |
| 6,251,127 | B1 | 6/2001 | Biel | 607/88 |
| 6,273,884 | B1 | 8/2001 | Altshuler et al. | 606/9 |
| 6,273,885 | B1 | 8/2001 | Koop et al. | 606/9 |
| 6,290,713 | B1 | 9/2001 | Russell | 607/88 |
| 6,306,130 | B1 | 10/2001 | Anderson et al. | 606/27 |
| 6,350,275 | B1 * | 2/2002 | Vreman et al. | 607/88 |
| 6,383,176 | B1 | 5/2002 | Connors et al. | 606/9 |
| 6,443,978 | B1 * | 9/2002 | Zharov | 607/91 |
| 6,494,900 | B1 * | 12/2002 | Salansky et al. | 607/89 |
| 6,524,329 | B1 * | 2/2003 | Benedict | 607/88 |
| 6,537,302 | B1 * | 3/2003 | Thiberg | 607/88 |
| 6,569,155 | B1 | 5/2003 | Connors et al. | 606/9 |
| 6,596,016 | B1 * | 7/2003 | Vreman et al. | 607/88 |
| 6,860,896 | B2 * | 3/2005 | Leber et al. | 607/1 |
| 2003/0040738 | A1 * | 2/2003 | Ruiz et al. | 606/5 |
| 2004/0044384 | A1 * | 3/2004 | Leber et al. | 607/88 |
| 2004/0111132 | A1 * | 6/2004 | Shenderova et al. | 607/88 |
| 2005/0004631 | A1 * | 1/2005 | Benedict | 607/88 |

FOREIGN PATENT DOCUMENTS

| | | |
|---|---|---|
| WO | WO 86/02783 | 5/1986 |
| WO | WO 95/15725 | 6/1995 |
| WO | WO 96/22813 | 8/1996 |
| WO | WO 98/24514 | 6/1998 |
| WO | WO 98/51235 | 11/1998 |
| WO | WO 99/11324 | 3/1999 |

OTHER PUBLICATIONS

Bartley et al., "An Experimental Study to Compare Methods of Eyelash Ablation," *Ophthalmology*, vol. 94, 1987, pp. 1286-1289.

J.L. Boulnois, "Photophysical Processes in Recent Medical Laser Developments: a Review," *Lasers in Medical Science*, vol. 1, 1986, pp. 47-64.

Finkelstein et al., "Epilation of Hair-Bearing Urethral Grafts Using the Neodymium: YAG Surgical Laser," *J. Urology*, vol. 146, 1991, pp. 840-842.

Grossman et al., "Prospective Evaluation of the Argon Laser in the Treatment of Trichiasis," *Ophthalmic Surgery*, vol. 23, 1992, pp. 183-189.

Grossman et al., "Experimental Comparison of Laser and CryoSurgical Cilia Destruction," *Ophthalmic Surgery*, vol. 23, 1992, pp. 179-182.

Kuriloff et al., "Pharyngoesophageal Hair Growth: the role of Laser Epilation,": *Case Reports*, vol. 98, 1988, pp. 342-345.

* cited by examiner

METHOD AND SYSTEM FOR CONTROLLED SPATIALLY-SELECTIVE EPIDERMAL PIGMENTATION PHOTOTHERAPY WITH UVA LEDS

RELATED APPLICATION

This patent application claims the benefit of U.S. Provisional Application No. 60/432,935, filed Dec. 12, 2002, which is incorporated herein by reference.

FIELD OF THE INVENTION

The present invention provides for spatially selective phototherapy using LEDs.

BACKGROUND

A number of diseases, medical or trauma conditions give rise to cosmetically undesirable pigmentary variation in human skin. Scars, temporary or permanent hypo- and hyper-pigmentation, striae (stretch marks), leukoderma, poikiloderma of Civatte, etc., are examples of conditions in which a melanin pigmentation cosmetic defect is presented by at least one component of the condition. A variety of approaches have been used to reduce the contrast between pigment variation regions, including chemical etches ("peel"), dermabrasion, laser ablation, and UV light sources.

Prior approaches for dealing with these conditions included removing the abnormally pigmented skin, or a portion of such skin with the goal of promoting new growth that contains cosmetically desirable "natural" pigmentation. Another approach provided for treating skin with UV light sources to promote the formation of melanin in melanin-deficient skin.

Ablative laser skin resurfacing, chemical peels and dermabrasion are examples of some approaches used for removing skin. UV lamps and excimer laser therapies are examples of some types of UV light sources.

Prior approaches have suffered from a lack of good control over the pigment induction. One shortcoming frequently associated with removing abnormally pigmented skin is that pigment-deficient areas of skin frequently exhibit resistance to melanogenesis or pigment induction. Thus, even after removing a portion of the pigment-deficient area of skin, and generating new growth of skin, the pigment deficiency frequently persists. In connection with providing UV treatment to pigment deficient skin, difficulties are also realized in that the spatial localization of the treatment is difficult to control and results in less than desirable outcomes.

BRIEF DESCRIPTION OF DRAWINGS

FIG. 1B shows details of an electric console.

DETAILED DESCRIPTION

Generally desirable characteristics of a phototherapeutic approach to pigmentary induction would include: (i) production of a temporary-to-permanent pigmentary darkening in various skin phototypes; and (ii) an ability to target discrete and localized non-uniformities and "blend" them to produce a more uniform pigment background. An embodiment herein provides for controlling the exposure to light, so that the treatment does not result in just increasing an overall pigment background by a uniform amount (e.g. merely increasing a base level of all pigment in a treatment area). For example, an embodiment herein can provide for a relatively large area UV exposure with some type of masking, or directing a UV point source at a specific local target.

Figure 1A:
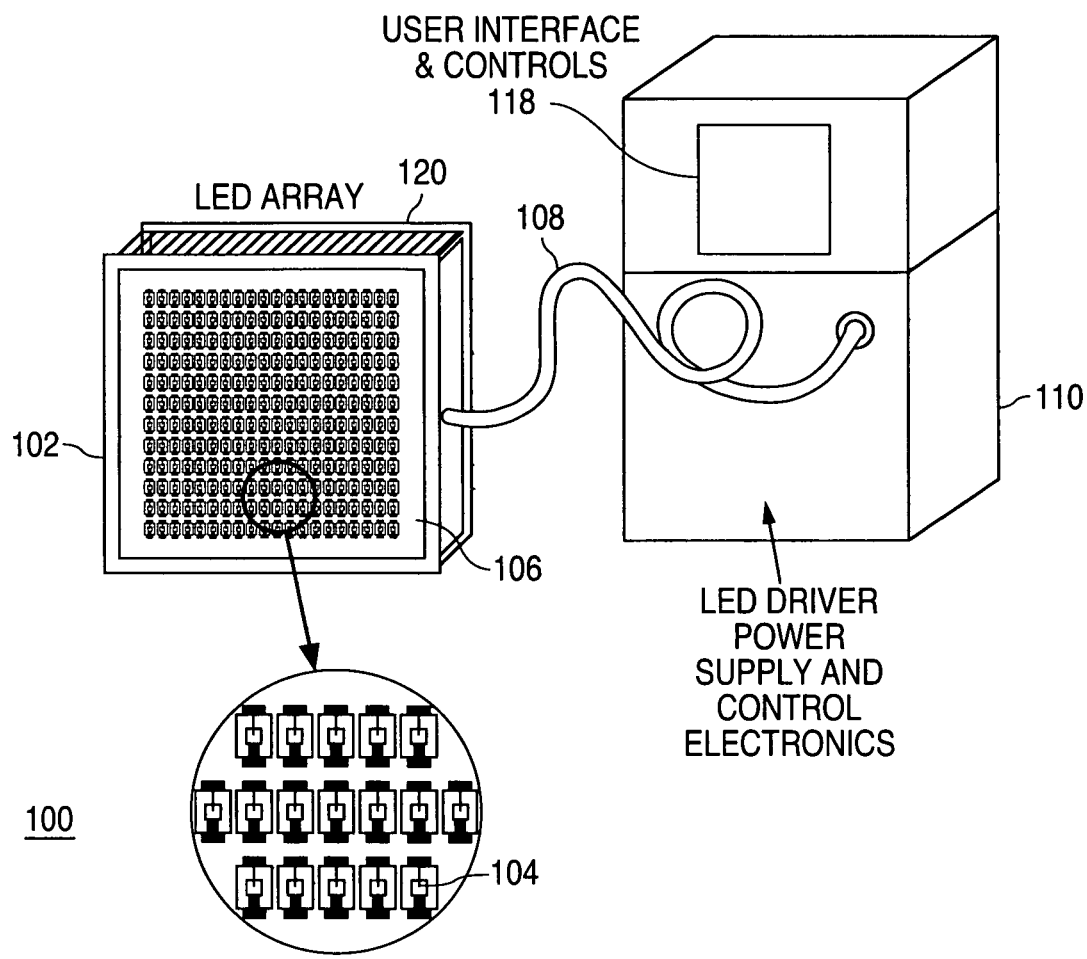
FIGS. 1A–1B are diagrams showing views of an embodiment of a system herein.

A system of an embodiment of the present invention is shown in FIG. 1A. The system 100 includes a rigid or flexible array module 102 of LEDs 104 arranged such that a high density of LEDs can be achieved. The array module 102 is placed in near, or close, contact with the skin, whereby the LEDs 104 are optically coupled with the skin such that light emitted from the LED is incident on the skin being treated. The LEDs 104 are electrically configured to allow for low voltage, high current operation. The array module 102 is electrically isolated from the patient in case direct contact with the array module 102 occurs. This isolation could be achieved by providing an electrically insulating, but optically transmissive material over the LEDs 104.

The array module 102 includes a surface structure 106 to which the LEDs are mounted. This surface structure could be formed on a printed circuit board which contains conductive paths from the LEDs 104 to a larger passive heat sink, or active cooler 120, such as water channel cooled plate. Typical heat loading from dissipation by LEDs in such an array is <1W/cm$^2$. For arrays containing 1000 or more LEDs, such heat loading can be in the 100's of Watts.

Figure 1B:
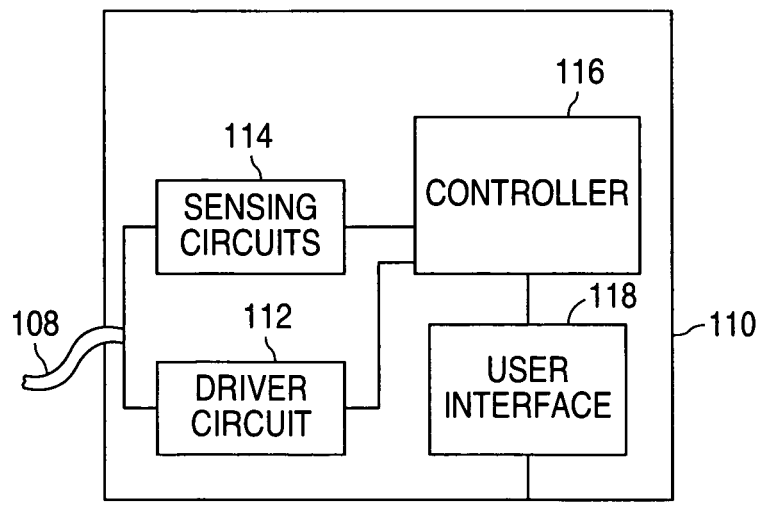

An umbilical supply cord 108 containing the driving current lines, temperature sensor, optical sensor and potentially low flow water for active cooling connects the array module 102 and LEDs 104 with the drive electronics console 110. Additional details of the console are shown in FIG. 1B. The console 110 contains a power supply, or driver circuit, 112 capable of providing for pulsed or CW operation of the LEDs 104, by controlling the electrical energy supplied to the LEDs. The console 110 also contains sensing circuits 114 to monitor the current, the array temperature, and the light flux. Further as will be discussed in more detail below a processor or controller 116 of the console operates to analyze the information from sensor or detectors in the array module 102, and to control the amount of current generated to by the driver circuit 112 to drive individual LEDs 104. Additionally a user interface 118 is provided to allow a user to control different aspects of the operation. More details related to a general structure of an LED array module and a console used to supply light energy to a patient's skin are disclosed in commonly assigned pending U.S. patent application Ser. No. 10/422,261 entitled SYSTEM AND METHOD FOR TREATING EXPOSED TISSUE WITH LIGHT EMITTING DIODES filed Apr. 24, 2003, which is incorporated herein by reference in its entirety.

An embodiment herein provides cosmetically desirable pigmentation in the skin in a spatially and temporally controlled manner. Melanin synthesis in melanocytes, or "melanogenesis", refers to this process. Melanogenesis can take place as a photoprotective effect in response to UV radiation, and when it occurs in response to natural or artificial UV light, it is referred to as "tanning."

A distinct phenomenon associated with true melanogenesis also occurs upon exposure to UV and visible light. "Immediate pigment darkening" (IPD) is a transient oxidative change to the state of existing melanin, occurs mostly in darker skin phototypes. The persistence of IPD is hours to days, and is not clinically useful in itself for treating pigmentation cosmetic problems. Strong IPD in dark skin phototypes indicates that longer term (days to onset) melanogenesis will take place, and may serve as a clinical endpoint to pigmentation phototherapy. Additional discussion related to this issue is provided by, Kollias N, Malallah Y H, Al-Ajmi H, Baqer A, Johnson B E, Gonzales S. *Erythema and melanogenesis action spectra in heavily pigmented individuals as compared to fair-skinned Caucasians*, Photodermatol Photoimmunol Photomedicine 1996: 12: 183–188, which is incorporated herein by reference in its entirety.

Figure 2:
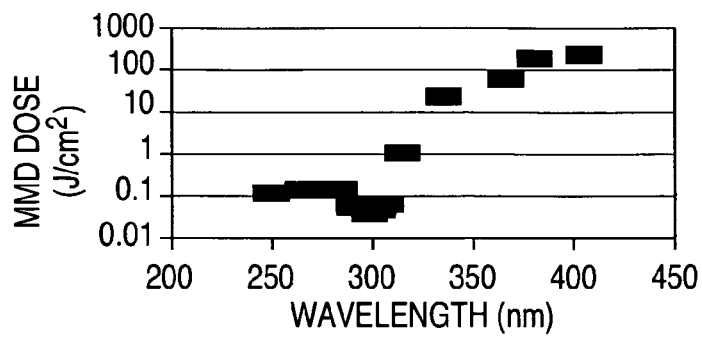
FIG. 2 is a graph showing the relationship between a minimum melanogensis dose and wavelength.

As shown in FIG. 2 there is a strong dependence between melanogenesis action and wavelength, with the threshold dose rising rapidly as the wavelength increases from the end of the UVB (~320 nm) into the blue (400 nm). Beyond 400 nm, there is very little melanogenesis. The graph shown in FIG. 2 shows the minimum melanogenic dose (MMD) for light skin people along the vertical axis. The MMD is on the order of $100J/cm^2$ for 365 nm, $1-10J/cm^2$ for 315 nm, and $0.1J/cm^2$ around 300 nm. As has been previously observed, the MMD is roughly independent of skin phototype. See e.g., Parrish J A, Jaenicke K F, Anderson R R. *Erythema and melanogenesis action spectra of normal human skin*. Photochem Photobiol Vol. 36, pp 187–191, 1982, which is incorporated herein by reference, in its entirety.

From a practical standpoint one must recognize that there are some issues that need to be addressed in connection with using LEDs. At present LED performance is best in the visible and infrared, and falls rapidly at the shorter wavelengths of the UVA range. An example of a high performance UV LED commercially available are the NSHU550A and NSHU590A from Nichia Corporation, Japan. These parts provide 2.0 and 1.4 mW of UVA light centered at 375 nm, respectively. In fact, at present, commercial devices below 360 nm are not readily available. Choosing appropriate LED devices becomes a trade-off between shorter wavelengths that are more effective, and longer wavelengths at which efficient and practical LED devices can be obtained.

Reasonably high flux devices with a central emission band below 400 nm and above 365 nm can be obtained using some currently available LEDs. The MMD's in this band are in the low 100's of $J/cm^2$. For treatments that are reasonably short duration (<1 hr total), and are somewhat above the MMD (for example, $500J/cm^2$), irradiances of at least 100 $mW/cm^2$ are desired. Close packed arrays of sub-400 nm devices are commercially available (one example the Shark OTL-395A-5-10-66 available from OptoTech, Inc. Wheeling, Ill.). At distances of a few millimeters, these arrays provide measured irradiances of up to 200 mW in an approximately 1 $cm^2$ emitting area. The wavelength center of this array was measured to be 395 nm. An arrangement of such LED arrays in close proximity to a person's skin can be used to produce a uniformly high irradiance of near-UVA, sub-400 nm illumination field. Similarly, the LEDs provided by Nichia Corporation, which can be obtained in 5 mm diameter packages, can be used to produce as much as 5 $mW/cm^2$ of 375 nm light on skin. The approximately 20× reduction in irradiance with these LEDs compared to the example above is partially offset by the factor of 3 decrease in the MMD required at this somewhat shorter wavelength, as is illustrated in FIG. 2.

Experiments have been performed using a 410 nm LED arrays to treat a patient's face. While melanogenesis is not expected to occur in this waveband, treatment of a dark phototype skin showed obvious IPD after 30 minutes of treatment at approximately 80 $mW/cm^2$ ($140J/cm^2$ dose). IPD maximum sensitivity falls between 320 and 380 nm.

Figure 3:
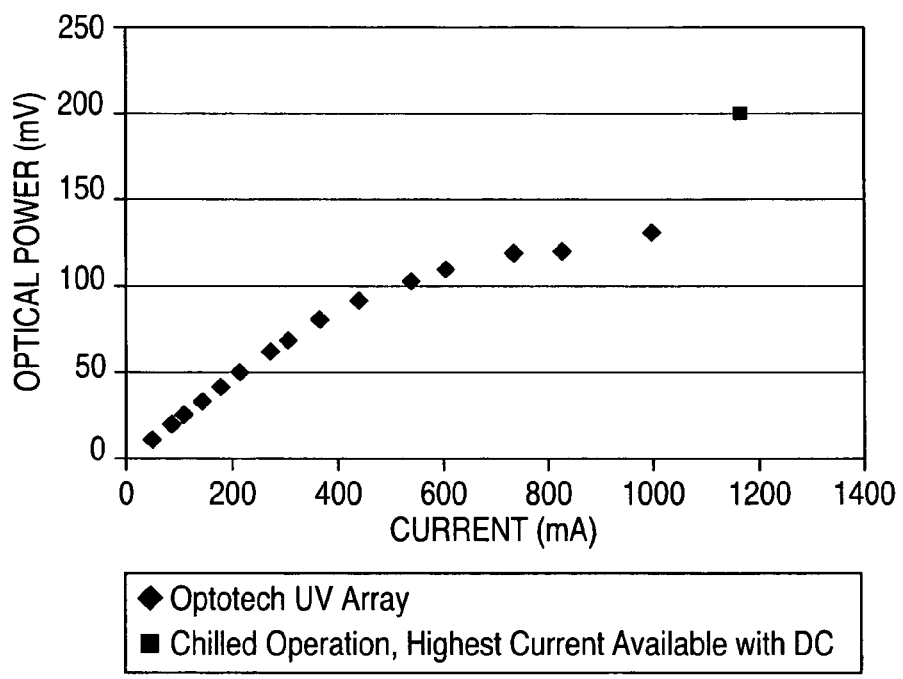
FIG. 3 shows an optical power output for an LED array relative to driving current.

FIG. 3 shows the measured output for an OptoTech 395 Shark LED array. At least 200 mW of power at a wavelength of 395 nm is emitted from an array measuring approximately 1 $cm^2$, when aggressive cooling of the array substrate is provided. This cooling allows the array to be driven past nominal operation current limits to produce up to several hundred mW of potentially melanogenic radiation.

Implementation of system 100 with an array module 102 using 395 nm LEDs arrays should reach the MMD in less than 1 hour of treatment time over a broad treatment area. In embodiment the array module 102 would use approximately 1000 individual LED devices in an array that is designed to treat approximately 50 $cm^2$ area of the face or back, and drives the entire array at approximately 6A and 45V, or ~300W.

Figure 4:
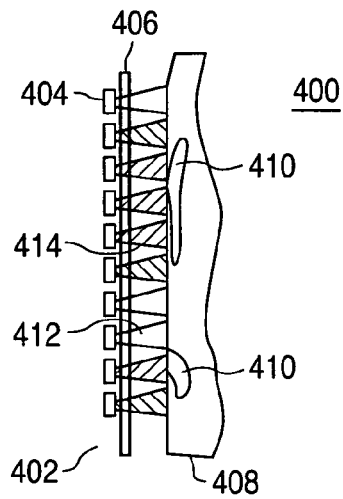
FIG. 4 shows a portion of a selectively controllable LED array.

FIG. 4 shows a cross sectional view of a portion of an array module 402 of a system 400 where spatially controlled UVA is applied to skin. This array module 402 in conjunction with the electronic console, which supplies driving electrical current to the array module, would provide spatially addressable direct UVA treatment. The LEDs 404 are provided which would be mounted to a printed circuit board (not shown). A optically transmissive layer 406 can be positioned adjacent to the emitting area of the LEDs. The embodiment shown in FIG. 4 allows one to spatially tailor the exposure or dose in such a way as to create a custom pigmentation induction profile. This is accomplished by making each individual LEDs 404 addressable with continuously adjustable drive current for LED or groups of LEDs. Addressability of each LED requires significantly more traces on the array printed circuit board or substrate to which the LEDs are mounted and could in some implementations reduce the density that LEDs can be placed in the array.

The consequence is that the delivered irradiance is lower than a system where all of the LEDS are subject to a single control and drive current. This reduction depends on the array size, and can be reduced by addressing entire rows or small blocks or regions of LEDs, rather than individual devices.

The addressable UVA LED array 402 is positioned so that it is adjacent to the patient's skin 408 which is to be treated. The white regions 410 in the skin represent low melanin content in skin. The areas 412 and 414 represent irradiance which would be delivered from an LED when current is supplied to the particular LED to drive the device. As shown the darker areas 414 correspond to LEDs which would receive higher current and emit higher energy amounts of UVA to the pigment deficient areas of skin 410. In this embodiment, advance knowledge of the desired spatial profile of the treatment dosage or irradiance is required. In operation, an area of the patient's skin which is to be treated would be mapped, and the information would be input to the controller 116 in the electronic console 110. The controller 116 would then cause the driver circuit 112 of the electronic console 110 to output current to regions of LEDS which are positioned to emit UVA to the pigment deficient area of the skin, and other areas which are not pigment deficient would not receive a driving current. It should be noted that depending on the actual implementation each addressable LED region could consist or one or more LEDs.

Ideally the LED array would be such that it is capable of providing very high resolution, so that it can provide UVA to those areas which are pigment deficient. In some cases, pigment deficient areas can be as narrow as 1 mm wide.

Figure 5:
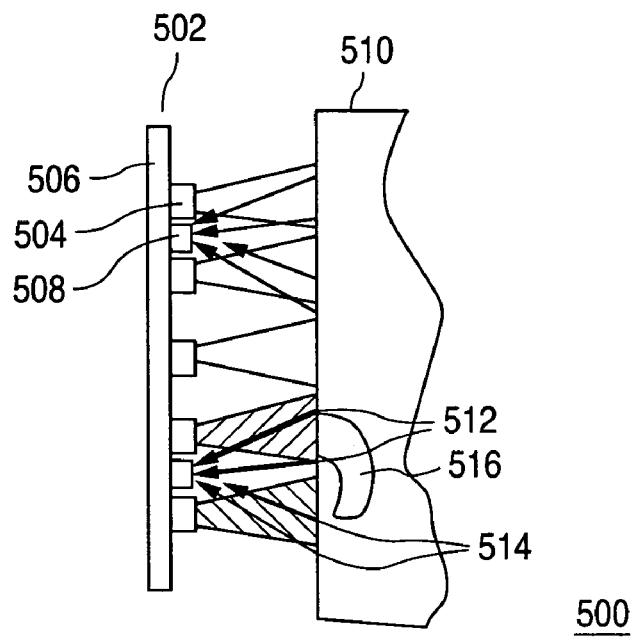
FIG. 5 shows a portion of a selectively controllable LED array with photodetectors.
Figure 8:
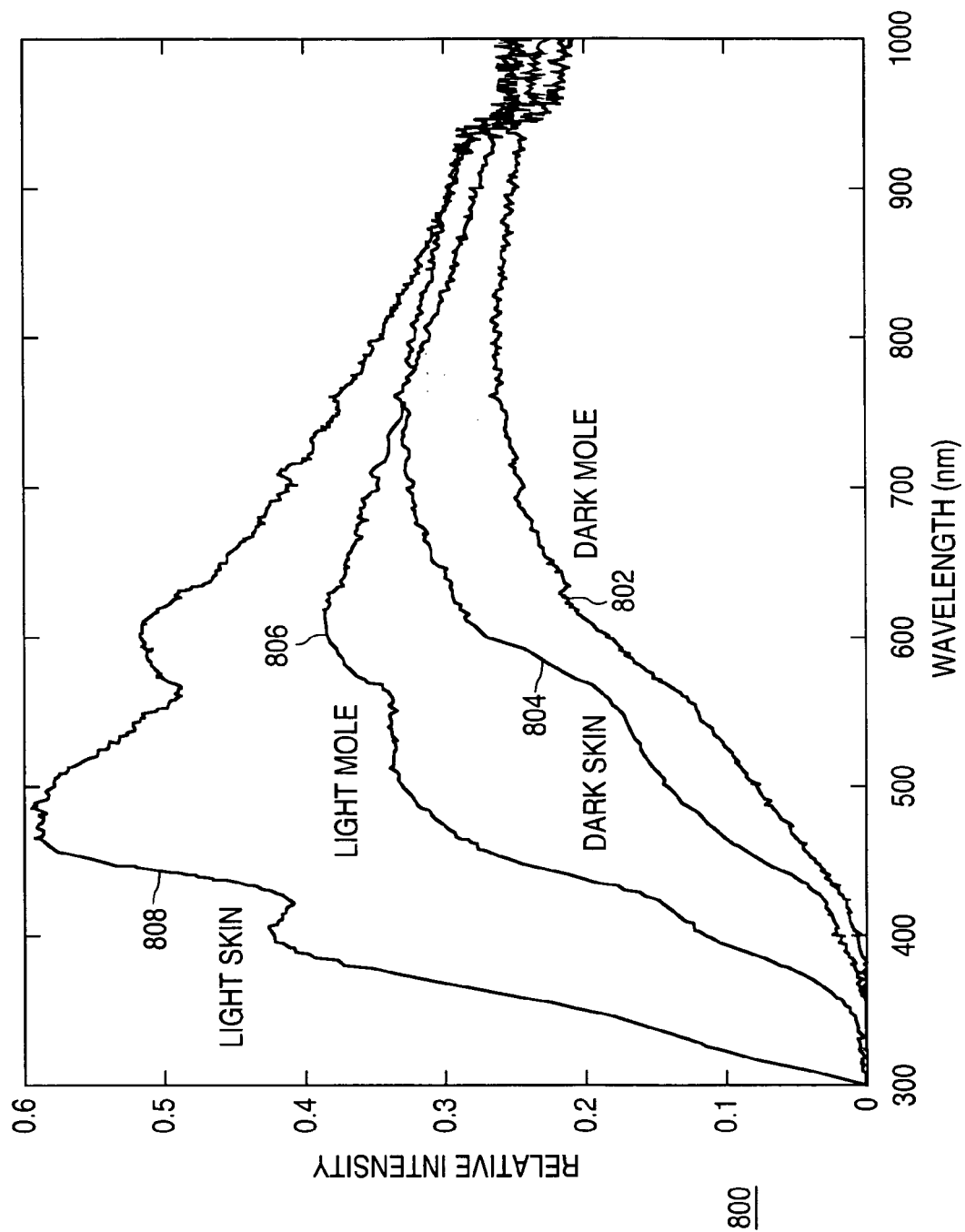
FIG. 8 is a graph showing a relationship between skin pigmentation and an intensity of back scattered light.

FIG. 5 shows a cross sectional view of a portion of a different embodiment of an array module 502 of a system 500 where spatially controlled UVA is applied to skin. In this embodiment, the individually addressable array of LEDs is similar to that described above in connection with FIG. 4, but additionally included are photodetectors. FIG. 5 shows the individual LEDs 504 mounted to structure 506. As discussed above the structure 506 could be printed circuit board or other structure which provides electrical connections to the LEDs. In addition to LEDs 504 photodetectors 508 are shown. These photodetectors 508 are chosen to be sensitive to light backscattered by the skin 510. The LEDs 504 are positioned in near-contact mode such that they are optically coupled with the skin. As is known, different amounts of pigmentation can have a large effect on the spectral remittance (the amount of light backscattered from the skin.) FIG. 8 shows a graph 800 which demonstrates this sensitivity. (The graph 800 reflects known characteristics of the spectral remittance of skin.) Lines 802, 804, 806 and 808 show the relative intensity of back scattered light different areas of skin pigmentation such as dark mole, dark skin, light mole and light skin respectively. As shown, skin bearing different pigmented structures exhibits greatly different diffuse reflectance values at various wavelengths. For UV LEDs operating therapeutically below 375 nm, it may be necessary to add some sensing LEDs operating at longer wavelengths. The individual photodetectors 508 will sense the amount of light reflected of the skin, and signals corresponding the amount of light received at each of the photodetectors 508 will then be transmitted by electrical connections to the structure 506, and then via the umbilical chord 108 to the electric console 110. The processor 116 in the electric console 110 can then can the correlate the amount of reflected light with an amount of pigment in skin near the detector 508. Based on the amount of reflected light the controller 116 will then cause the driver circuit to supply an amount of current to LEDs 504 which are in the region associated with the particular photodetector 508. In the system 500, as shown in FIG. 5, the arrows 512 represent the direction and strength of the light reflected from the low pigment area 516, and the arrows 514 represent the direction and strength of light reflected from higher pigment areas of skin 510. As shown, more light will be reflected from low areas of pigmentation, and as a result the controller will cause the driver circuit to supply more current to LEDs in these low pigment areas.

The light from LEDs 504 may serve as the backscattered light that the photodetector 508 senses. In this case, the lack of pigment causes a higher proportion of the UVA light to be backscattered relative to the more UVA-absorbing pigment bearing regions Another embodiment could provide for populating the LED array with a number of alternate wavelength LEDs, where the wavelength of the alternate LEDs could be chosen for maximum contrast in the amount of absorption between pigmented and hypo-pigmented regions (400–550 nm light would be suitable candidate for this purpose—see FIG. 2)

In one embodiment the photodetector signals serve as the basis of a control loop for determining the exposure for a given area of skin, and an array of LEDs delivers the appropriate dose profile. In one version, the feedback or servo mechanism is determined at the beginning of treatment, and is not necessarily dynamic. That is, the initial pigment profile determines the spatial profile of the treatment dosing. In still another embodiment, instead of measuring differences only between initial pigmentation, the photodetector array senses dynamically the changes in remittance due to immediate pigment darkening IPD detection, which can then be used to determine the end point of exposure. This can be done in a spatially localized way, as above, or it can be used to determine the end of the overall treatment.

Further, it is helpful to recognize that the spectral remittance for dark and light human skin is different. Indeed some prior works have specifically compared dark and light skin phototypes, and developed data showing the difference in the relative amount of UVA-visible light which is backscattered. See e.g. R. R. Anderson and J. A. Parrish, *Optical Properties of Human Skin*, p. 159–193, The Science of Photomedicine, 1982, which is incorporated herein by reference in its entirety. See also the data shown in FIG. 8 for diffuse reflectance for different skin pigmentation levels.

Figure 6:
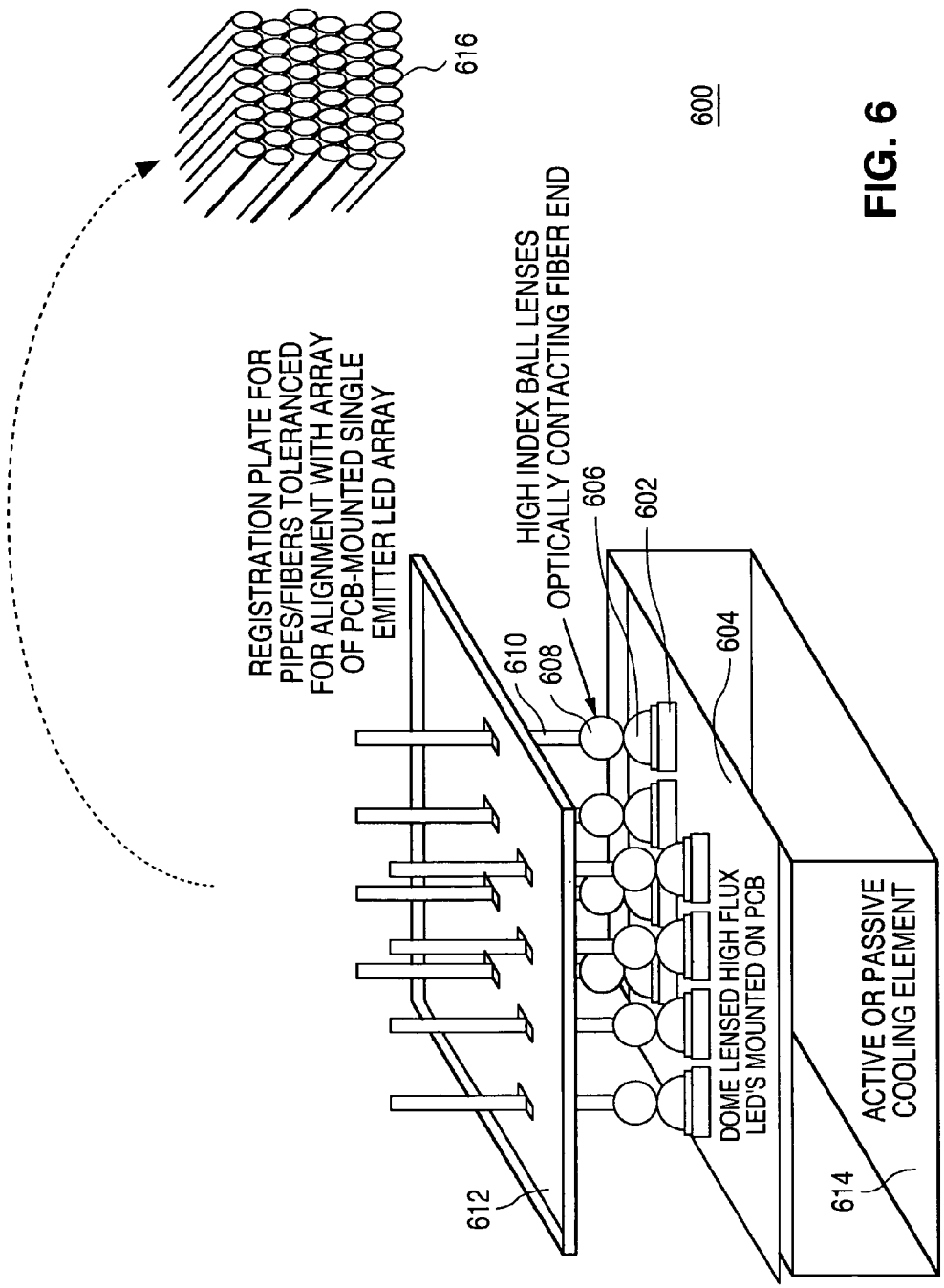
FIG. 6 shows an LED array coupled with fibers.

FIG. 6 is a view of another embodiment herein. In this embodiment an array or arrays LEDS 602 are mounted to a printed circuit board 604 as discussed above. A dome lens 606 would then be provided with each of the LEDs 602. A high index ball lens 608 would then be used to couple the light from LED 602 into a corresponding fiber 610. A registration plate 612 for the fibers 610 can be used to align the fibers 610 with the array of LEDs 602. A cooling element 614 can be mounted adjacent to the printed circuit board for cooling the LEDs 602, and by providing a temperature conducting path to the LEDs 606. The fibers 610 can then be configured to provide a fiber bundle 616 which could be housed in a hand piece (not shown). Additional aspects of coupling light from an LED into a fiber, and related issues are discussed in more detail in commonly assigned pending U.S. patent application Ser. No. 10/171,101, Spooner et al., "Concentration of Divergent Light from Light Emitting Diodes into Therapeutic Light Energy", filed 12 Jun. 2002, which is incorporated herein by reference in its entirety.

In the system 600 of FIG. 6, the array or arrays of LEDs 602 can be located remotely from the skin, and coupled with high efficiency into individual fibers, which are subsequently bundled 616 to produce a broad area high irradiance illumination handpiece or other optical delivery system. One advantage is that by concentrating the light into fibers 610, a larger maximum treatment irradiance can be obtained (generally at the cost of overall efficiency).

The bundle 610 is then placed in near contact with the skin. Actual contact of the bundle or associated delivery against the skin could desirably be minimized. UVA-driven melanogenesis is very strongly dependent on circulatory oxygen. That is, pressing on skin with, say, a window, during phototreatment with a UVA source could drop the response by as much as 10×. See e.g., Auletta M, Gange R W, Tan O T, Matzinger E. *Effect of Cutaneous Hypoxia upon erthyma and pigment responses to UVA, UVB and PUVA (8-MOP+UVA) in Human Skin.* J Invest Dermatol 86:

649–652, 1986; which is incorporated herein by reference in its entirety, and discusses the effect of circulatory oxygen on phototreatment.

Figure 7:
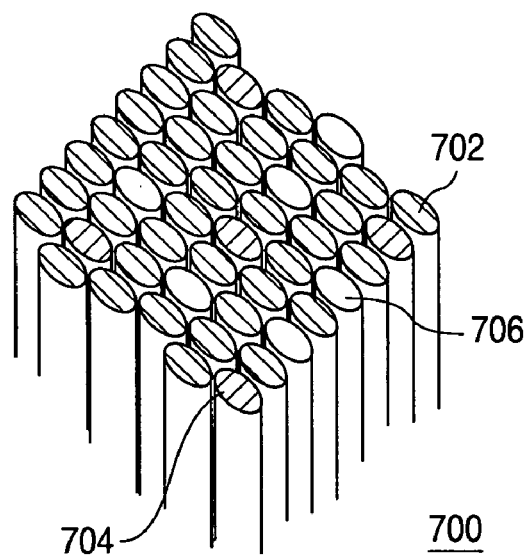
FIG. 7 shows a fiber bundle couple with photodetectors, and different LEDs.

FIG. 7 shows an alternative embodiment 700 of the fiber bundle 616 discussed above. The fiber bundle 700 provides in for emitting UVA from LEDs in conjunction with using photodetectors which would be located remotely on a printed circuit board and provide for optical sensing. As shown in FIG. 7 the fibers 702 would be coupled to UVA emitting LEDs. Some of the fibers 706 are not coupled to LEDs, but rather are connected to photosensors or photodetectors. Some fibers 704 may also be connected to a green or other wavelength LED to enhance the sensitivity of the reflectance signal, as discussed above. An advantage of the reflectance sensing and treatment fiber bundle 700 is that can provide better spatial resolution than may be achievable with an addressable array. The required space between LEDs for printed circuit board traces for each device would no longer place a limit on the density with which emitting devices (output coupled fibers, in this case) can be positioned. In this embodiment the position of the detector coupled fibers and the individual LED illuminator fibers would then be mapped, and a controller in the electrical console would determine how much current should be used to drive the individual LEDs or regions of LEDs based on the reflected light received by the fibers which are coupled to the photodetectors.

Coupling visible LEDs into large core fibers can result in up to 30% of the light emitted from a domed LED being captured. As multi-milliWatt LEDs in the 365–375 nm range come available, it will be possible to create bundles using fiber coupling to produce irradiances at the bundle output of tens of milliWatts/cm$^2$, sufficient to induce melanogenesis in reasonable treatment times.

An additional advantage of the overall fiber bundle approach is that the light treatment handpiece or delivery system can be small and located far from the actual electronics and light generating array(s).

Additionally a bundle of fibers or light pipes can be further concentrated, with substantial loss of power, by a secondary guide or reflector. Advantages of this approach include the ability to treat small regions by a hand-applied tip, and the use of even higher irradiances than direct arrays or bundled fibers (as much as 100 mW/cm$^2$ of 365–375 nm may be possible.

Although specific embodiments and methods of the present invention are shown and described herein, this invention is not to be limited by these methods and embodiments. Rather, the scope of the invention is to be defined by the following claims and their equivalents.

What is claimed is:

1. A method for treating an area of tissue, where the area of tissue includes a plurality of different sub-areas of tissue which have different characteristics:
   providing a plurality of light emitting devices optically coupled with the area of tissue, wherein the light emitting devices are configured into different regions, where different sub-areas of tissue having different characteristics correspond to different regions of light emitting diodes;
   sensing an amount of light reflected from each of the different sub-areas;
   driving a first region of the plurality of light emitting devices to output a first light treatment to a first sub-area of tissue, wherein the first light treatment is determined based on a first amount of light reflected from the first sub-area; and
   driving a second region of the plurality of light emitting devices to output a second light treatment to a second sub-area of tissue, wherein the second light treatment is determined based on a second amount of light reflected from the second sub-area of tissue.

2. The method of claim 1, wherein the first light treatment induces a first amount of tanning in the first sub-area.

3. The method of claim 2, wherein the second light treatment induces a second amount of tanning in the second sub-area.

4. The method of claim 1, wherein the first light treatment includes light having a wavelength below 400 nm.

5. The method of claim 1, wherein the first light treatment provides for an irradiance at least 100 mW/cm$^2$ for the first sub-area.

6. The method of 1, wherein the first light treatment provides for a first level of irradiance for the first sub-area, and the second light treatment provides for a second level or irradiance for the second sub-area and the second level of irradiance is less that the first level or irradiance.

7. The method of claim 1, further including driving the plurality of light emitting devices to induce tanning in the area of tissue, such that the tanning operates to provide for a more uniform distribution pigmentation in the area tissue, than was present in the area of tissue prior to the induced tanning.

8. A method for treating an area of tissue, where the area of tissue includes a plurality of different sub-areas of tissue which have different amounts of pigmentation:
   sensing an amount of light reflected from each of the plurality of different sub-areas; and
   applying a light treatment to the area of tissue, based on the amount of light reflected from each of the plurality of different sub-areas, wherein the light treatment operates to reduce differences in the amount of pigmentation in different sub-areas of tissue.

9. The method of claim 8, wherein the applying the light treatment includes:
   generating a first amount of light to apply a first light treatment to a first sub-area of the area of tissue; and
   generating a second amount of light to apply a second light treatment to a second sub-area of the area of tissue.

10. The method of claim 8, wherein the applying the light treatment includes:
    applying a first amount of light energy to a first group of sub-areas of tissue of the area of tissue, where the first group of sub-areas of tissue have less pigmentation, than a second group of sub-areas of tissue to which the first amount of light energy is not applied.

11. The method of claim 10, wherein the first amount of light energy induces a first amount of tanning in the first group of sub-areas of tissue.

12. The method of claim 10, wherein the first amount of light energy includes light having a wavelength below 400 nm.

13. The method of claim 10, wherein the first amount of light energy provides for an irradiance at least 100 mW/cm$^2$ for the first group of sub-areas.

* * * * *